United States Patent [19]
Greff et al.

[11] Patent Number: 6,086,906
[45] Date of Patent: Jul. 11, 2000

[54] CYANOACRYLATE COMPOSITIONS COMPRISING AN ANTIMICROBIAL AGENT

[75] Inventors: Richard J. Greff, St. Pete Beach, Fla.; Michael M. Byram, Colorado Springs, Colo.

[73] Assignee: MedLogic Global Corporation, Colorado Springs, Colo.

[21] Appl. No.: 08/912,681

[22] Filed: Aug. 18, 1997

Related U.S. Application Data

[63] Continuation-in-part of application No. 08/781,409, Jan. 10, 1997, Pat. No. 5,684,042.

[51] Int. Cl.⁷ ..................................................... A61L 25/00
[52] U.S. Cl. ........................................ 424/407; 424/78.37
[58] Field of Search .............................. 424/78.25, 78.37, 424/407; 606/214, 215

[56] References Cited

U.S. PATENT DOCUMENTS

| | | |
|---|---|---|
| 2,784,127 | 3/1957 | Joyner et al. . |
| 3,223,083 | 12/1965 | Cobey ...................................... 606/214 |
| 3,524,537 | 8/1970 | Winter ...................................... 606/214 |
| 4,323,557 | 4/1982 | Rosso et al. ........................... 424/78.25 |
| 4,374,126 | 2/1983 | Cardarelli et al. . |
| 4,542,012 | 9/1985 | Dell . |
| 4,713,235 | 12/1987 | Krall . |
| 4,978,527 | 12/1990 | Brink et al. . |
| 4,994,542 | 2/1991 | Matsuda et al. . |
| 5,051,256 | 9/1991 | Barnes . |
| 5,069,907 | 12/1991 | Mixon et al. . |
| 5,306,490 | 4/1994 | Barley, Jr. ............................ 424/78.35 |
| 5,328,687 | 7/1994 | Leung et al. . |
| 5,350,573 | 9/1994 | Goldberb et al. ..................... 424/78.35 |
| 5,383,899 | 1/1995 | Hammerslag ............................ 606/214 |
| 5,480,935 | 1/1996 | Greff et al. . |
| 5,547,662 | 8/1996 | Khan et al. . |
| 5,580,565 | 12/1996 | Tighe et al. ............................. 424/400 |

FOREIGN PATENT DOCUMENTS

WO 96/23532   8/1996   WIPO .

OTHER PUBLICATIONS

Ritter, M.A., et al., "Retrospective Evalution of an indophor–Incorporated Antimicrobial Plastic Adhesive Wound Drape"—Clinical Orthopedics and Related Research, (1986) pp. 307–308.

Sidorova, et al., Preventing Incompentence of Uterine Suture after Ceasarian Section, Akusherstvo I. Ginekologiia, (Mar. 1989) 3:30–33 (Abstract Only).

Timokhina, V.I., "Biological Properties of New Adhesion Compositions of Medical Purpose", Biodestruktiruysshchve Polim. Mater. (1982) 55–61 (Abstract Only).

C. Cable—Handbook of Adhesive Bonding 21–1 1970.

Skeist—Handbook of Adhesives Coover, Jr. pp. 409–413 1970.

*Primary Examiner*—Peter F. Kulkosky
*Attorney, Agent, or Firm*—Burns, Doane, Swecker & Mathis LLP

[57] ABSTRACT

Disclosed are cyanoacrylate compositions comprising a compatible antimicrobial agent and, in particular, a compatible iodine containing antimicrobial agent. These compositions provide for in situ formation of an antimicrobial polymeric cyanoacrylate film on mammalian skin.

18 Claims, No Drawings

CYANOACRYLATE COMPOSITIONS COMPRISING AN ANTIMICROBIAL AGENT

CROSS-REFERENCE TO RELATED APPLICATIONS

This application is a continuation-in-part of U.S. Ser. No. 08/781,409 filed Jan. 10, 1997, now U.S. Pat. No. 5,684,042 which issued on Nov. 4, 1997, which application is incorporated herein by reference in its entirety.

BACKGROUND OF THE INVENTION

1. Field of the Invention

This invention is directed to cyanoacrylate prepolymer compositions comprising a compatible antimicrobial agent and, in particular, an iodine containing antimicrobial agent. These compositions provide for in situ formation of antimicrobial polymeric cyanoacrylate films on mammalian skin which films are useful as wound dressings, wound bandages, surgical incise drapes, wound closure materials which replace or are an adjunct to sutures, and the like.

This invention is also directed to kits of parts comprising such prepolymer compositions and an applicator means for applying the composition to mammalian skin.

References

The following publications, patent applications and patents are cited in this application as superscript numbers:

[1] Hawkins, et al., *Surgical Adhesive Compositions*, U.S. Pat. No. 3,591,676, issued Jul. 6, 1971

[2] Halpern, et al., *Adhesive for Living Tissue*, U.S. Pat. No. 3,667,472, issued Jun. 6, 1972

[3] McIntire, et al., *Process for the Preparation of Poly(α-Cyanoacrylates)*, U.S. Pat. No. 3,654,239, issued Apr. 4, 1972

[4] Barley, et al., *Methods for Treating Non-Suturable Wounds by Use of Cyanoacrylate Adhesives*, International Patent Application Publication No. WO 93/25196, published Dec. 23, 1993

[5] Barley, et al., *Methods for Treating Suturable Wounds by Use of Sutures and Cyanoacrylate Adhesives*, U.S. Pat. No. 5,254,132, issued Oct. 19, 1993

[6] Barley, et al., *Methods for Reducing Skin Irritation From Artificial Devices by Use of Cyanoacrylate Adhesives*, U.S. Pat. No. 5,653,789, issued Aug. 5, 1997

[7] Rabinowitz, et al., *Method of Surgically Bonding Tissue Together*, U.S. Pat. No. 3,527,224, issued Sep. 8, 1970

[8] Kronenthal, et al., *Surgical Adhesives*, U.S. Pat. No. 3,995,641, issued Dec. 7, 1976

[9] Davydov, et al., *Medical Adhesive*, U.S. Pat. No. 4,035,334, issued Jul. 12, 1977

[10] Waniczek, et al., *Stabilized Cyanoacrylate Adhesives Containing Bis-Trialkylsilyl Esters of Sulfuric Acid*, U.S. Pat. No. 4,650,826, issued Mar. 17, 1987

[11] Askill, et al., *"Methods for Draping Surgical Incision Sites"* U.S. Pat. No. 5,730,994 which issued on Mar. 24, 1998 filed Jan. 10, 1997

[12] Greff, et al., *Cyanoacrylate Adhesive Compositions*, U.S. Pat. No. 5,480,935, issued Jan. 2, 1996

[13] Hagen, et al., *"A Comparison of Two Skin Preps Used in Cardiac Surgical Procedures"*, AORN Journal, 62(3):393–402 (1995)

[14] Ritter, et al., *"Retrospective Evaluation of an Iodophor-incorporated Antimicrobial Plastic Adhesive Wound Drape"*, Clinical Orthopedics and Related Research, pp. 307–308 (1988)

[15] Osuna, et al., *"Comparison of an Antimicrobial Adhesive Drape and Povidone-Iodine Preoperative Skin Preparation in Dogs"*, Veterinary Surgery, 21(6):458–462 (1992)

[16] O'Sullivan, et al., *High Viscosity Cyanoacrylate Adhesive Compositions, and Process for Their Preparation*, U.S. Pat. No. 4,038,345, issued Jul. 26, 1977

[17] Beller, et al., *Process for the Preparation of Iodine-Polyvinylpyrrolidone by Dry Mixing*, U.S. Pat. No. 2,706,701, issued Apr. 19, 1955

[18] Hosmer, *Process of Stabilizing Polyvinylpyrrolidone*, U.S. Pat. No. 2,826,532, issued Mar. 11, 1958

[19] Siggin, *Preparation of Iodine Polyvinylpyrrolidone Adducts*, U.S. Pat. No. 2,900,305, issued Aug. 18, 1958

[20] Joyner, et al., *Plasticized Monomeric Adhesive Compositions and Articles Prepared Therefrom*, U.S. Pat. No. 2,784,127, issued Mar. 5, 1957

[21] Columbus, et al., *Adhesive Cyanoacrylate Compositions with Reduced Adhesion to Skin*, U.S. Pat. No. 4,444,933, issued Apr. 24, 1984

[22] Leung, et al., *Biocompatible Monomer and Polymer Compositions*, U.S. Pat. No. 5,328,687, issued Jul. 12, 1994

[23] Byram, et al., *Use of Cyanoacrylate Adhesive Compositions to Inhibit Acute Radiation-Induced Skin Damage*, U.S. Pat. No. 5,554,365, issued Sep. 10, 1996.

[24] Leplyanin, *"Medical and Surgical Adhesive Composition and Process for Its Preparation"*, International Application Publication No. WO 96/23532 published Aug. 8, 1996

[25] Tighe, et al., *"Use of Cyanoacrylate Adhesives For Providing A Protective Barrier Film For The Skin"*, U.S. Pat. No. 5,580,565, issued on Dec. 3, 1996.

[26] Cardarelli, et al., *"Film Forming Antimicrobial Material"*, U.S. Pat. No. 4,374,126, issued Feb. 15, 1983

[27] Barnes, *"Biocidal Complex and Dressing Formed Therefrom"*, U.S. Pat. No. 5,051,256, issued Sep. 24, 1991

[28] Dell, *"Film-Forming Composition Containing an Antimicrobial Agent and Methods"*, U.S. Pat. No. 4,542,012, issued Sep. 17, 1985

[29] Brink, et al., *"Film-Forming Emulsion Containing Iodine and Methods of Use"*, U.S. Pat. No. 5,173,291, issued Dec. 22, 1992

[30] Khan, et al., *"Preparation of a Skin Surface for a Surgical Procedure"*, U.S. Pat. No. 5,547,662, issued Aug. 20, 1996

[31] Blum, et al., *In vitro Determination of the Antimicrobial Properties of Two Cyanoacrylate Preparations*, J. Dent. Res., 54(3):500–503 (1975)

All of the above publications, patent applications and patents are herein incorporated by reference in their entirety to the same extent as if each individual publication, patent application or patent was specifically and individually indicated to be incorporated by reference in its entirety.

2. State of the Art

Cyanoacrylate esters have been disclosed for a variety of topical uses on mammalian skin including use as a replacement or adjunct for sutures or staples in closing the dermal layer of an incision after surgery.[1,2,5] Other disclosed topical uses include use as a hemostat[3], use in covering small non-suturable wounds on skin surfaces[4], use in inhibiting surface skin irritation arising from friction between the skin surface and artificial devices such as tapes, prosthetic devices, casts, etc.[6] and use in inhibiting acute radiation-induced skin damage.[23] Still another topical use of cyanoacrylate esters is its use in the in situ formation of a surgical incise drape.[11] In each case, when topically applied to mammalian skin, the cyanoacrylate rapidly polymerizes, typically within a minute, to form a coherent polymeric film which strongly adheres to the skin.

Cyanoacrylate esters suggested for such uses include the following structures:

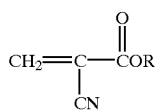

I wherein R is an alkyl or other suitable substituent. Such cyanoacrylate esters are disclosed in, for example, U.S. Pat. Nos. 3,527,224; 3,591,676; 3,667,472; 3,995,641; 4,035,334; and 4,650,826.[1,2,7-10]

Cyanoacrylate ester compositions for topical skin application typically are formulated to contain both a plasticizer to enhance flexibility of the resulting polymeric film and a polymerization inhibitor to avoid premature polymerization of the composition. When employed topically on mammalian skin, Greff et al.[12] disclose that the cyanoacrylate composition preferably employs from about 50 to about 500 ppm sulfur dioxide as the polymerization inhibitor and from about 18–25 weight percent of a biocompatible plasticizer such as dioctyl phthalate.

Notwithstanding the beneficial properties associated with such cyanoacrylate ester compositions and their suitability for topical applications, these compositions do not possess a sufficiently broad spectrum of antimicrobial activity including activity against microbial spores[31] and, accordingly, cannot assure reductions in microbial populations on mammalian skin surface either under or adjacent a polymeric cyanoacrylate film formed in situ on the skin.

Many of the uses of cyanoacrylate ester compositions enumerated above would, however, significantly benefit by a broad spectrum of antimicrobial property in the polymer film. For instance, covering small non-suturable wounds on skin surfaces with a polymeric cyanoacrylate film having a broad spectrum of antimicrobial activity would mitigate against possible wound infection. Likewise, when used as a surgical (incise) drape, such films would reduce microbial populations under and adjacent the drape including those at the incision site and, accordingly, would reduce the risk of post-operative infection. Such is the basic premise of commercial surgical drapes containing an antimicrobial agent impregnated directly into the drape or an adhesive layer attached thereto where it was hoped that this agent would be released onto the skin surface to inhibit microbial growth.[13, 14] Osuna, et al.[15] report, however, that when the antimicrobial agent is incorporated into the adhesive layer, the adhesive does not release sufficient amounts of the impregnated agent to be, by itself, antimicrobial. Without being limited to any theory, it is believed that the antimicrobial agent is too strongly bound onto/into the adhesive to be released onto the skin and/or that there is insufficient skin surface contact between the adhesive and the skin to effect release of a sufficient amount of antimicrobial agent.

As noted above, cyanoacrylate esters do not possess broad antimicrobial activity and, accordingly, incorporation of broad antimicrobial properties into the cyanoacrylate polymeric film necessitates, of course, that an antimicrobially effective amount of a broad spectrum antimicrobial agent be incorporated into the prepolymeric cyanoacrylate composition and that sufficient amounts of this agent be released from the polymeric cyanoacrylate film onto the skin to achieve an antimicrobial effect. The incorporation of such an antimicrobial agent into the cyanoacrylate composition is problematic at best because several disparate criteria must be simultaneously met. First, the antimicrobial agent must be soluble or dispersible in the cyanoacrylate composition at the concentrations necessary to effect antimicrobial properties. Second, the antimicrobial agent employed must not cause premature polymerization of the cyanoacrylate ester composition. Third, the antimicrobial agent employed must not prevent in situ polymerization of the cyanoacrylate composition when applied to the skin. Fourth, the antimicrobial agent must be compatible with the intended use of the polymeric film by not inhibiting formation of a flexible, durable film. Fifth, the impregnated antimicrobial agent must be released from the polymerized film in situ on the patient's skin in sufficient amounts to be antimicrobial.

Because of these disparate properties, many conventional antimicrobial agents are unsuitable for use in the prepolymeric compositions of this invention and typically the prior art has incorporated an antimicrobial agent into a solution or emulsion of the formed polymer or by direct mixing in the polymer melt (Mixon, U.S. Pat. No. 5,069,907).

When the antimicrobial agent is incorporated into the solution emulsion, after placement on the patient's skin and subsequent evaporation of the solvent, a polymer film is formed which film is permeated with the antimicrobial agent.[26,28-29] Since the polymer is preformed prior to application to the skin, these solutions/emulsions reduce the effective adherence of the polymer film to the skin and, accordingly, could lead to premature lifting or removal of the film from the skin. Moreover, the use of water and other solvents in the emulsion or solution can lead to slow drying times for the film with the concurrent difficulty in determining when or if the solvent has evaporated sufficiently to provide a polymer film on the patient's skin.

In view of the clear benefits associated with the incorporation of an antimicrobial agent directly into the monomeric cyanoacrylate composition, there is an ongoing need to formulate a cyanoacrylate composition comprising a broad spectrum antimicrobial agent.

SUMMARY OF THE INVENTION

This invention is directed to cyanoacrylate ester compositions comprising an antimicrobially effective amount of a complex of iodine molecules with a biocompatible polymer. These compositions provide for in situ formation of an antimicrobial polymeric cyanoacrylate film on mammalian skin. The specific antimicrobial iodine complex employed is compatible with the cyanoacrylate composition insofar as the antimicrobial complex neither causes premature polymerization nor prevents polymerization of the monomer, rather a flexible and durable polymeric film is formed in situ on mammalian skin by this composition. Moreover, in vitro assays evidence that the antimicrobial agent is released from the polymeric film in antimicrobially effective amounts thereby imparting antimicrobial properties to the polymeric film.

Accordingly, in one of its composition aspects, this invention is directed to an antimicrobial cyanoacrylate composition which comprises:

(a) a polymerizable cyanoacrylate ester; and (b) an antimicrobially effective amount of a complex of iodine molecules with a biocompatible polymer.

Preferably, the polymerizable cyanoacrylate ester is a polymerizable monomer or reactive oligomer of a cyanoacrylate ester. Such monomers and reactive oligomers are sometimes referred to herein simply as "prepolymers" and, in monomeric form, are preferably represented by formula I:

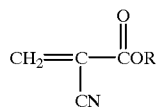

wherein R is selected from the group consisting of:
alkyl of 1 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

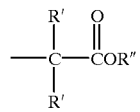

wherein each R' is independently selected from the group consisting of:
hydrogen and methyl, and R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

More preferably, in the cyanoacrylate esters of formula I, R is alkyl of from 2 to 10 carbon atoms and still more preferably alkyl of from 4 to 8 carbon atoms. Even more preferably, R is butyl, pentyl or octyl and most preferably, R is n-butyl.

Antimicrobial complexes of iodine molecules with a biocompatible polymer preferably include polyvinylpyrrolidone polymers which are also referred to under the common name of Povidone or PVP (commercially available from BASF, Mt. Olive, N.J., USA), copolymers of vinylpyrrolidone and vinyl acetate, copolymers of vinylpyrrolidone and vinyl acetate cross-linked with polyisocyanates, copolymers of vinylpyrrolidone and vinyl functionalities, polymers of pyrrolidone[27] and the like. Preferably, the iodine containing polymer is Povidone Iodine which is commercially available from a number of sources.

The antimicrobial cyanoacrylate compositions preferably further comprise an effective amount of a polymerization inhibitor and a biocompatible plasticizer. The preferred polymerization inhibitor is sulfur dioxide which is preferably employed at from about 50 to about 500 ppm, and preferably 200 to 500 ppm, based on the total weight of the composition absent the antimicrobial agent. The preferred biocompatible plasticizer is dioctyl phthalate which is preferably employed at from about 18 to 25 weight percent based on the total weight of the composition absent the antimicrobial agent.

This invention is also directed to kits useful for applying the antimicrobial cyanoacrylate compositions described herein onto mammalian skin. In particular, such a kit of parts comprises (a) a container comprising therein an antimicrobial prepolymeric composition as described above and (b) an applicator means for applying the composition onto mammalian skin.

DETAILED DESCRIPTION OF THE PREFERRED EMBODIMENTS

This invention is directed, in part, to cyanoacrylate compositions comprising an antimicrobially effective amount of a compatible iodine containing antimicrobial agent. However, prior to discussing this invention in further detail, the following terms will first be defined.

Definitions

As used herein, the following terms have the following meanings:

The term "cyanoacrylate ester compositions" or "cyanoacrylate compositions" refers to polymerizable formulations comprising polymerizable cyanoacrylate ester monomers and/or oligomers which, in their monomeric form, are preferably compounds represented by formula I as described above.

More preferably, in formula I, R is an alkyl group of from 2 to 10 carbon atoms including, by way of example, ethyl, n-propyl, iso-propyl, n-butyl, isobutyl, sec-butyl, n-pentyl, iso-pentyl, n-hexyl, iso-hexyl, 2-ethylhexyl, n-heptyl, n-octyl, nonyl, and decyl. More preferably, R is butyl, pentyl or octyl and most preferably, R is n-butyl. Mixtures of such compounds can also be employed.

Polymerizable cyanoacrylate esters are known in the art and are described in, for example, U.S. Pat. Nos. 3,527,224; 3,591,676; 3,667,472; 3,995,641; 4,035,334; and 4,650,826[1,2,7-10] the disclosures of each are incorporated herein by reference in their entirety.

A particularly preferred cyanoacrylate ester for use in the invention is n-butyl-2-cyanoacrylate.

The polymerizable cyanoacrylate ester compositions described herein rapidly polymerize in the presence of water vapor or tissue protein, and the n-butyl-cyanoacrylate bonds human skin tissue without causing histotoxicity or cytotoxicity.

Such polymerizable cyanoacrylate esters are sometimes referred to herein as prepolymers and compositions comprising such esters are sometimes referred to herein as prepolymer compositions.

The term "a biocompatible polymer" refers to polymers which, as iodine complexes (adducts), are compatible with in vivo applications of cyanoacrylate ester compositions onto mammalian skin including human skin. Representative polymers include polyvinylpyrrolidone, copolymers comprising polyvinylpyrrolidone which is optionally crosslinked, and the like. Suitable copolymers include copolymers of polyvinylpyrrolidone and vinyl acetate or other vinyl compounds which copolymers are optionally crosslinked with a polyisocyanate. The molecular weight of these polymers is not critical with number average molecular weights ranging from about 10,000 to about 1,000,000 and preferably from 30,000 to 300,000 being preferred.

The term "a complex of iodine molecules with a biocompatible polymer" refers to an antimicrobial complex formed by the addition of iodine ($I_2$) to the biocompatible polymer. Such complexes are well known in the art and the resulting complex typically comprises both available iodine and iodine anions. These complexes, on contact with mammalian skin, are antimicrobial apparently by providing for a source of antimicrobial iodine. In any event, such complexes are employed only as starting materials herein and, by themselves, do not form a part of this invention.

These complexes are sometimes referred to herein simply by the term "iodine/polymer complexes". Such iodine/polymer complexes are distinguished from antibiotics which are naturally derived materials from either bacteria or fungi and whose mode of action is to interfere with bacterial processes resulting in bacterial death. Contrarily, the complexes used in this invention are indiscriminate in destroying any microbes including fungi, viruses and bacteria apparently by release of iodine into the microbes and, accordingly, are properly referred to as antimicrobial agents. Surprising, it has been found that of the antimicrobial agents tested, only the iodine/polymer complexes are compatible in cyanoacrylate compositions. In fact, elemental (solid) iodine is incompatible with cyanoacrylate compositions because the addition of elemental iodine renders such compositions non-polymerizable on mammalian skin. Accordingly, complexation of the iodine with the biocompatible polymer is apparently essential for compatibility with the cyanoacrylate composition.

A preferred iodine/polymer complex for use in the compositions of this invention is a polyvinylpyrrolidone iodine complex which is described in, for example, U.S. Pat. Nos. 2,706,701, 2,826,532 and 2,900,305[17-19] as well as at pp. 1106–1107 of the Tenth Edition of the Merck Index, Published by Merck & Co., Rahway, N.J., USA (1983) the disclosures of which are incorporated herein by reference in their entirety. This complex is commercially available under the name "povidone-iodine" from BASF, Mt. Olive, N.J., USA.

The term "biocompatible plasticizer" refers to any material which is soluble or dispersible in the cyanoacrylate composition, which increases the flexibility of the resulting polymer film coating on the skin surface, and which, in the amounts employed, is compatible with the skin as measured by the lack of moderate to severe skin irritation. Suitable plasticizers are well known in the art and include those disclosed in U.S. Pat. Nos. 2,784,127[20] and 4,444,933[21] the disclosures of both of which are incorporated herein by reference in their entirety. Specific plasticizers include, by way of example only, acetyl tri-n-butyl citrate (preferably ~20 weight percent or less), acetyl trihexyl citrate (preferably ~20 weight percent or less) butyl benzyl phthalate, dibutyl phthalate, dioctylphthalate, n-butyryl tri-n-hexyl citrate, diethylene glycol dibenzoate (preferably ~20 weight percent or less) and the like. The particular biocompatible plasticizer employed is not critical and preferred plasticizers include dioctylphthalate.

The term "polymerization inhibitor" refers to conventional inhibitors of cyanoacrylate esters including materials such as sulfur dioxide, glacial acetic acid, and the like. The polymerization inhibitor is typically employed in amounts effective to inhibit polymerization until application onto the mammalian skin. Because of its compatibility with topical skin applications, the polymerization inhibitor is preferably sulfur dioxide which is preferably employed at from about 50 to 500 ppm, preferably 200 to 500 ppm, based on the total weight of the composition. Other preferred polymerization inhibitors include glacial acetic acid, free radical inhibitors (e.g., hydroquinones) and the like which can be used alone or in combination with $SO_2$.

The term "antimicrobial agent" refers to agents which destroy microbes (i.e., bacteria, fungi, viruses and microbial spores) thereby preventing their development and pathogenic action.

Compositions

This invention is based on the novel and unexpected discovery that the iodine/polymer complexes described herein are compatible with cyanoacrylate esters forming a prepolymer composition which, upon polymerization, provides for an antimicrobial cyanoacrylate polymeric film. Compatibility is assessed by the fact that these complexes are dispersible in the cyanoacrylate ester composition at antimicrobially effective concentrations and when so employed, do not cause premature polymerization of the cyanoacrylate ester composition and do not prevent effective polymerization of the cyanoacrylate ester composition when applied to mammalian skin. Moreover, the polymerizable cyanoacrylate ester composition comprising such complexes forms a flexible, durable polymeric film having the complex incorporated therein which complex is released from the film in sufficient amounts to provide antimicrobial properties to the film.

As shown in the examples below, many other conventional antimicrobial agents, when added to the cyanoacrylate ester composition cause polymerization of this composition as evidenced by gel formation within 24 hours of such addition or, in the case of elemental iodine, prevent in situ polymerization of the cyanoacrylate ester composition on mammalian skin. Accordingly, such agents are not compatible with the cyanoacrylate ester compositions.

The compositions of this invention are prepared by adding the iodine/polymer complex to the cyanoacrylate ester composition. The iodine/polymer complex is preferably added as the commercially available solid composition rather than as the commercially available aqueous or ethanolic solution insofar as the solution can cause premature polymerization of the cyanoacrylate ester which is apparently due to solvent's effects. Accordingly, the compositions described herein are preferably free of added solvents (e.g., water, organic solvents such as chloroform, methanol, ethanol, toluene, ethyl acetate, hexane, etc.).

Upon addition of the solid iodine/polymer complex to the cyanoacrylate prepolymer composition, the resulting system is thoroughly mixed to obtain a homogeneous suspension.

The amount of iodine/polymer complex added to the cyanoacrylate composition is a sufficient amount such that the resulting polymeric film is antimicrobial. Preferably, from about 5 to about 40 weight percent of the iodine/polymer complex and more preferably from about 10 to 25 weight percent is added to the cyanoacrylate composition based on the total weight of the composition.

The specific amount of iodine/polymer complex required to effect antimicrobial properties in the resulting polymeric film can be readily measured by conventional in vitro assays measuring zones of microbial growth inhibition around the film. Zones of inhibition of at least 1 millimeter and preferably 3 millimeters from the edge of the film when tested in the manner of Example 2 below evidence that the polymeric film is antimicrobial. Assessing the amount of iodine/polymer complex required in the polymeric film to effect such a zone of inhibition is well within the skill of the art.

The composition of the antimicrobial complex and the cyanoacrylate ester can be formulated to a specific viscosity to meet disparate demands for the intended application of the composition. For example, relatively low viscosities are often preferred where application is to be made to a large surface area (e.g., abdominal surfaces). This preference results from the fact that these forms are less viscous and, accordingly, will permit more facile large surface area application of a thin film. Contrarily, where application is to be made to a specific position on the skin (e.g., elbow surfaces, knee surfaces and the like), higher viscosity compositions, including those containing thixotropic materials, are preferred to prevent "running" of the compositions to unintended locations.

Accordingly, these compositions have a viscosity of from about 2 to 50,000 centipoise at 20° C. For low viscosity applications, viscosity ranges of from about 2 to 1,500 centipoise at 20° C. are preferred. More preferably, the cyanoacrylate ester employed in the composition is almost entirely in monomeric form and the composition has a viscosity of from about 5 to about 500 centipoise at 20° C.

A thickening agent is optionally employed to increase the viscosity of the composition which thickening agent is any biocompatible material which increases the viscosity of the composition. Suitable thickening agents include, by way of example, polymethyl methacrylate (PMMA) or other preformed polymers soluble or dispersible in the composition, a suspending agent such as fumed silica and the like, with PMMA being preferred. Fumed silica is particularly useful in producing a gel for topical application having a viscosity of from about 1500 to 50,000. Suitable thickening agents for the cyanoacrylate compositions described herein also include a polymer of the alkyl cyanoacrylate as disclosed in U.S. Pat. Nos. 3,654,239[3] and 4,038,345[16] both of which are incorporated herein by reference in their entirety.

Thickening agents are deemed to be biocompatible if they are soluble or dispersible in the composition and are compatible with the skin as measured by the lack of moderate to severe skin irritation.

The cyanoacrylate composition preferably includes a biocompatible plasticizer and such plasticizers are preferably included from about 10 to 30 weight percent and more preferably from about 18 to 25 weight percent based on the weight of the composition absent the antimicrobial agent. A particularly preferred biocompatible plasticizer for use in the compositions described herein is dioctylphthalate.

Additionally, the cyanoacrylate compositions described herein preferably include a polymerization inhibitor in an effective amount to inhibit premature polymerization of the composition. In a particularly preferred embodiment, this inhibitor is sulfur dioxide which is employed at from about 50 to 500 ppm based on the total weight of the composition absent the antimicrobial agent. Another preferred inhibitor is glacial acetic acid which is employed in an amount effective to inhibit premature polymerization.

The cyanoacrylate ester compositions may additionally contain one or more optional additives such as colorants, perfumes, anti-diffusion agents, rubber modifiers, modifying agents, etc. In practice, each of these optional additives should be both miscible and compatible with the cyanoacrylate composition and the resulting polymer. Compatible additives are those that do not prevent the use of the cyanoacrylates in the manner described herein.

In general, colorants are added so that the polymer layer formed on the skin will contain a discrete and discernable color. Perfumes are added to provide a pleasant smell to the formulation. Rubber modifiers are added to further enhance the flexibility of the resulting polymer layer. The amount of each of these optional additives employed in the composition is an amount necessary to achieve the desired effect.

Additionally, the cyanoacrylate composition can optionally comprise a formaldehyde scavenger compound such as those described by Leung, et al.[22] The use of such scavengers has been suggested as enhancing internal in vivo applications of cyanoacrylates.

Still further, it is contemplated that the cyanoacrylate composition can optionally comprise an acrylic monomer that will act as a polymeric plasticizer when it copolymerizes with the cyanoacrylate composition.[24]

Utility

The methods described herein are useful in forming in situ a broad spectrum antimicrobial polymeric film on the skin surface of a mammalian patient. Such mammalian patients preferably include humans as well as, for example, domestic animals such as horses, cows, dogs, sheep, cats, etc.

The polymeric film finds particular utility in inhibiting microbial contamination thereunder and in the areas immediately adjacent thereto. Accordingly, such polymeric films can be used to topically cover small non-suturable wounds on skin surfaces which wounds do not penetrate through the dermal layer of the skin as in the manner described in Barley, et al.[4] When so employed, the antimicrobial cyanoacrylate composition is applied over the small non-suturable wound. Upon polymerization, an antimicrobial polymeric film is formed over the wound which provides for broad spectrum antimicrobial properties at the wound surface while also preventing exogenous contaminants from entering the wound.

Additionally, the polymeric films formed from the antimicrobial cyanoacrylate compositions described herein can also be used in the in situ formation of a surgical incise drape in the manner described by Askill, et al.[11] When so employed, the in situ formed film strongly adheres to the mammalian skin surface to provide for a surgical incise drape which does not lift during surgery and has broad spectrum antimicrobial properties.

When used as either a small wound covering or as a surgical incise drape, the antimicrobial polymeric film will only adhere to the skin for a period of about 1–4 days after which time it sloughs off. This occurs because the cyanoacrylate polymer adheres only to the uppermost portion of the epidermal layer which is continuously in the process of being sloughed off and replaced by the underlying cells. Accordingly, the antimicrobial cyanoacrylate film need not be removed after in situ formation. However, if removal of the polymeric film is required, such can be accomplished with a material such as acetone (nail polish remover).

Other utilities for the compositions of this invention include their use to form polymeric hemostatic films[3], use to form polymeric films in inhibiting surface skin irritation arising from friction between the skin surface and artificial devices such as tapes, prosthetic devices, casts, etc.[6], use in forming polymeric films in inhibiting acute radiation-induced skin damage[23], and use in treating incontinence and areas adjacent to stomas.[25]

Kits

In view of the many different uses for topical application onto mammalian skin, this invention also encompasses a kit of parts useful for applying the antimicrobial cyanoacrylate compositions described herein onto mammalian skin. In particular, such a kit of parts comprises (a) a container comprising therein an antimicrobial prepolymeric composition as described above and (b) an applicator means for applying the composition onto mammalian skin.

The container comprises any compatible material which stores the cyanoacrylate composition without degradation of the container or prematurely polymerizing the cyanoacrylate prepolymer. Such materials include, by way of example, inorganic materials such as Type 1 glass (including amber glass), ceramics, metals (e.g., aluminum, tin and tin coated tubes), etc. and organic materials such as inert polymers including polyolefins (e.g., high density polyethylene), fluorinated polyolefins, and the like. Examples of suitable containers include those recited in Bolduc, U.S. Pat. No. 5,154,320, which is incorporated herein by reference in it entirety.

Suitable applicator means include brushes, rollers, aerosols, swabs, foams (e.g., polyethylene foam) and the like. A particularly preferred applicator is described in U.S. Pat. No. 4,183,684.

In one embodiment, the container and applicator means are combined into a single article such as a brush affixed to the terminal portion of the container wherein means are employed to prevent premature release of the cyanoacrylate prepolymeric composition. For example, the brush may be overlayed with a removable imperable barrier. When application of the cyanoacrylate prepolymer composition is intended, the barrier is simply removed.

In another embodiment, the container and applicator means are separate articles designed to mate with each other. For example, the cyanoacrylate prepolymer composition could be stored in an amber vial sealed with a screw cap and the applicator means includes a screw mechanism which mates with the screw mechanism on the top of the vial. When application of the cyanoacrylate prepolymer composition is intended, the cap is removed from the vial and the applicator is attached. The particular container/applicator means are not critical and other such means are well within the scope of the skilled artisan including those set forth by Bolduc, U.S. Pat. No. 5,154,320.

The following examples illustrate certain embodiments of the invention but are not meant to limit the scope of the claims in any way.

EXAMPLES

In the examples below, all temperatures are in degrees celsius (unless otherwise indicated) and all percents are weight percent (also unless otherwise indicated) except for percent inhibition which is true mathematical percentage. Additionally, the following abbreviations have the following meanings. If an abbreviation is not defined, it has its generally accepted meaning.

| CFU | = | Colony forming units |
|---|---|---|
| conc. | = | concentration |
| flex. | = | flexibility |
| dur. | = | durability |
| mL | = | milliliters |
| mm | = | millimeters |
| ppm | = | parts per million |
| PVP-$I_2$ | = | polyvinylpyrrolidone iodine complex |
| SAB-DEX | = | Sabouraud Dextrose |
| TSA | = | trypticase soy agar |

EXAMPLE 1

The following example examines the compatibility of different antimicrobial agents in cyanoacrylate compositions. In particular, the composition employed monomeric n-butyl cyanoacrylate containing 100 ppm sulfur dioxide and 20 weight percent of dioctyl phthalate absent the antimicrobial agent. In each case, either 5 weight percent, 10 weight percent or 20 weight percent of the antimicrobial agent, based on the total weight of the composition, was added thereto and the properties of the resulting composition measured. The antimicrobial agents tested were elemental iodine, solid polyvinylpyrrolidone iodine, a 30% aqueous solution of polyvinylpyrrolidone iodine, silver nitrate, hexachlorophene, merbromin, tetracycline.HCl, tetracycline hydrate, and erythromycin (each of these antimicrobial agents were obtained from commercial sources).

The evaluation included assessing whether the antimicrobial agent was soluble or suspendable in the composition; whether the resulting composition cured upon contact with skin; whether curing provided for a polymeric film in situ on the skin; whether the polymeric film was flexible and durable. Solubility and suspendability were determined by conventional standards. The ability of the resulting composition to cure in situ upon application to skin was measured by applying the cyanoacrylate composition onto the upper arm of a male human subject and determining whether polymerization proceeded (up to 5 minutes) and, if so, the time required for polymerization. Film forming capabilities on the skin were assessed by visual evaluation. Durability was assessed by determining whether the film was retained on the skin surface for at least 24 hours and flexibility was measured by the ability of the film to be retained on the skin without cracking or peeling for at least 24 hours. The results of this evaluation are summarized in Table I below:

TABLE I

| Antimicrobial Agent | Conc. | Soluble | Curable | Film Formed | Flex. | Dur. |
|---|---|---|---|---|---|---|
| elemental iodine ($I_2$) | ~20% | partially | No (when tested for 5 minutes) | — | — | — |
| PVP-$I_2$ solid | 10% | no suspension[2] | Yes (30 seconds) | Yes | Yes | Yes |
| PVP-$I_2$ solution | 10% | no, gelled[1] | — | — | — | — |
| Silver nitrate | 5% | no, gelled[1] | — | — | — | — |
| Hexachlorophene | 5% | no, gelled[1] | — | — | — | — |
| Merbromin | 5% | no, gelled[1] | — | — | — | — |
| tetracycline HCl | 5% | no, gelled[1] | — | — | — | — |
| tetracycline hydrate | 5% | no, gelled[1] | — | — | — | — |
| Erythromycin | 5% | no, gelled[1] | — | — | — | — |

[1] gel formation within 24 hours of addition of the antimicrobial agent evidences premature polymerization of the cyanoacrylate. In such cases, the antimicrobial agent initiates polymerization.

[2] the mixture is readily resuspended with mild agitation. No gel formed over an 8 week period when stored at room temperature.

The above data demonstrates that of the antimicrobial agents tested, only polyvinylpyrrolidone iodine complex was compatible with the cyanoacrylate composition and, of the polyvinylpyrrolidone iodine complexes tested, only the solid form was compatible. Evidently, the solvent in the solution form of polyvinylpyrrolidone iodine complex initiated polymerization of the cyanoacrylate. Significantly, the suspension formed by the addition of solid polyvinylpyrrolidone iodine complex was curable in situ on human skin resulting in a flexible and durable polymeric film.

In addition to the above, polyvinylpyrrolidone is a well known biocompatible polymer thereby evidencing that such polymers, when completed with iodine, are suitable for use in the compositions described herein.

EXAMPLE 2

The following example was conducted to determine whether sufficient polyvinylpyrrolidone iodine complex was incorporated into the polymeric cyanoacrylate film formed in situ to render this film antimicrobial.

A. Preparation of the Inoculum

Specifically, the surfaces of two TSA plates, 100×15 mm, were inoculated with stock cultures (maintained on TSA slants) with the following microorganisms using a sterile inoculating loop: *Staphylococcus aureus* (ATCC No. 6538) and *Staphylococcus epidermidis* (ATCC No. 12228). The plates were incubated at 30° to 35° C. for 24 hours. The surfaces of two SAB-DEX agar plates were streaked with *Candida albicans* and incubated at 20–25° C. for 48 hours.

The cultures were harvested with sterile saline. Each culture suspension was collected in a sterile container and sufficient sterile saline was added to reduce the microbial count to obtain a working suspension of approximately $1\times10^8$ CFU's per mL.

The specific microorganisms recited above were selected for inclusion herein because they are common human skin pathogens (bacteria and fungus).

B. Inoculation of Plates

Each of the three test microorganisms was used to inoculate individual TSA plates by streaking them with sterile cotton tip applicators saturated with the appropriate suspension. The plates were allowed to dry.

C. Inhibition Study

Films of polymerized n-butyl cyanoacrylate comprising 0%, 10%, 15%, 20% or 30% iodine polyvinylpyrrolidone complex were formed on 25 mm filter disks and then cut into approximately 11 to 13 mm pieces. The pieces were placed in the center of the appropriate inoculated TSA plates. An untreated filter disk was cut into half, and one-half was placed in the center of the appropriate inoculated TSA plate and the other one-half was place in the center of non-inoculated TSA plates, to serve as a negative control. Two inoculated plates of each microorganism were also used as positive controls without the test article. These plates were then incubated for 3 days at 30° to 35° C. After incubation, the plates were removed and examined for any signs of microbial growth inhibition.

The results of this analysis are set forth in Tables II–IV below. The sample sizes reported are the portion of the sample actually in contact with the agar. The sizes of the zone of inhibition include the diameters of the entire zone including the test article size.

TABLE II

Results for *Staphylococcus aureus*

| SAMPLE:<br>n-butyl cyanoacrylate<br>comprising | SAMPLE SIZE[1]<br>(in mm) | ZONE OF<br>INHIBITION[1]<br>(in mm) |
| --- | --- | --- |
| 0% PVP-$I_2$ | 12 | 12 |
| 10% PVP-$I_2$ | 12 | 15 |
| 15% PVP-$I_2$ | 12.5 | 14 |
| 20% PVP-$I_2$ | 11.5 | 15.5 |
| 30% PVP-$I_2$ | 12.5 | 20 |
| Untreated Filter Disk | 13[2] | 13[2] |
| Negative Control | 13[2] | 13[2] |
| Positive Control | n/a | 0 |

TABLE III

Results for *Staphylococcus epidermis*

| SAMPLE:<br>n-butyl cyanoacrylate<br>comprising | SAMPLE SIZE[1]<br>(in mm) | ZONE OF<br>INHIBITION[1]<br>(in mm) |
| --- | --- | --- |
| 0% PVP-$I_2$ | 12 | 12 |
| 10% PVP-$I_2$ | 12.5 | 15 |
| 15% PVP-$I_2$ | 12 | 15.5 |
| 20% PVP-$I_2$ | 12.5 | 20.5 |
| 30% PVP-$I_2$ | 13 | 27.5 |
| Untreated Filter Disk | 13[2] | 13[2] |
| Negative Control | 13[2] | 13[2] |
| Positive Control | n/a | 0 |

TABLE IV

Results for *Candida albicans*

| SAMPLE:<br>n-butyl cyanoacrylate<br>comprising | SAMPLE SIZE[1]<br>(in mm) | ZONE OF<br>INHIBITION[1]<br>(in mm) |
| --- | --- | --- |
| 0% PVP-$I_2$ | 12 | 12 |
| 10% PVP-$I_2$ | 12.5 | 18.5 |
| 15% PVP-$I_2$ | 12.5 | 23 |
| 20% PVP-$I_2$ | 12.5 | 20.5 |
| 30% PVP-$I_2$ | 13 | 29.5 |
| Untreated Filter Disk | 13[2] | 13[2] |
| Negative Control | 13[2] | 13[2] |
| Positive Control | n/a | 0 |

[1]average of two runs
[2]single run only

The above data demonstrates that the compositions of this invention produce a polymeric cyanoacrylate film which have broad spectrum of antimicrobial activity. Based on these results, it is expected that these compositions would be antimicrobial when formed in situ on mammalian skin surfaces.

From the foregoing description, various modifications and changes in the composition and method will occur to those skilled in the art. All such modifications coming within the scope of the appended claims are intended to be included therein.

What is claimed is:

1. A kit of parts comprising:
   (a) a container comprising therein an antimicrobial pre-polymeric composition which comprises a mixture of:
      (i) a polymerizable cyanoacrylate ester; and
      (ii) an antimicrobially effective amount of a complex of iodine molecules with a biocompatible polymer;
   wherein said composition is capable of forming a film on mammalian skin surfaces; and (b) an applicator means for applying the composition onto mammalian skin.

2. A kit of parts according to claim 1 wherein the container and applicator means are combined into a single article.

3. A kit of parts according to claim 1 wherein the container and applicator means are separate articles.

4. The kit of according to claim 1 wherein the polymerizable cyanoacrylate ester is a polymerizable monomer or oligomer of a cyanoacrylate ester which, in monomeric form, is represented by formula I:

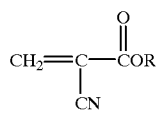

I wherein R is selected from the group consisting of:
   alkyl of 1 to 10 carbon atoms,
   alkenyl of 2 to 10 carbon atoms,
   cycloalkyl groups of from 5 to 8 carbon atoms,
   phenyl,
   2-ethoxyethyl,
   3-methoxybutyl,
   and a substituent of the formula:

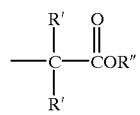

wherein each R' is independently selected from the group consisting of: hydrogen and methyl, and
R" is selected from the group consisting of:
   alkyl of from 1 to 6 carbon atoms,
   alkenyl of from 2 to 6 carbon atoms,
   alkynyl of from 2 to 6 carbon atoms,
   cycloalkyl of from 3 to 8 carbon atoms,
   aralkyl selected from the group consisting of benzyl, methylbenzyl and phenylethyl,
   phenyl, and
   phenyl substituted with 1 to 3 substituents selected from the group consisting of hydroxy, chloro, bromo, nitro, alkyl of 1 to 4 carbon atoms, and alkoxy of from 1 to 4 carbon atoms.

5. The kit of parts according to claim 1 wherein R is alkyl of from 4 to 10 carbon atoms.

6. The kit of parts according to claim 5 wherein R is alkyl of from 4 to 8 carbon atoms.

7. The kit of parts according to claim 6 wherein R is selected from the group consisting of butyl, pentyl or octyl.

8. The kit of parts according to claim 7 wherein R is n-butyl.

9. The kit of parts according to claim 1 wherein said complex of iodine molecules with a biocompatible polymer is polyvinylpyrrolidone iodine.

10. The kit of parts according to claim 1 wherein said antimicrobial prepolymeric composition further comprises a biocompatible plasticizer.

11. The kit of parts according to claim 10 wherein said biocompatible plasticizer is dioctyl phthalate or acetyl tri-n-butyl citrate.

12. The kit of parts according to claim 1 wherein said antimicrobial prepolymeric composition further comprises a polymerization inhibitor.

13. The kit of parts according to claim 12 wherein said polymerization inhibitor is $SO_2$.

14. The kit of parts according to claim 1 herein said antimicrobial prepolymeric composition comprises:

(a) a polymerizable cyanoacrylate ester which, in monomeric form, is represented by formula II:

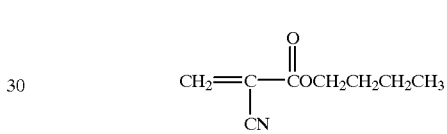

II (b) an antimicrobially effective amount of polyvinylpyrrolidone iodine complex.

15. The kit of parts according to claim 14 wherein said antimicrobial prepolymeric composition further comprises a biocompatible plasticizer.

16. The kit of parts according to claim 15 wherein said biocompatible plasticizer is dioctyl phthalate or acetyl tri-n-butyl citrate.

17. The kit of parts according to claim 14 wherein said antimicrobial prepolymeric composition further comprises a polymerization inhibitor.

18. The kit of parts according to claim 17 wherein said polymerization inhibitor is $SO_2$.

* * * * *